(12) United States Patent
Zhang (10) Patent No.: US 11,849,929 B2
(45) Date of Patent: Dec. 26, 2023

(54) PRESSURE GUIDE WIRE

(71) Applicant: BEIJING BYWAVE SENSING TECHNOLOGY CO., LTD., Beijing (CN)

(72) Inventor: Lizhe Zhang, Beijing (CN)

(73) Assignee: BEIJING BYWAVE SENSING TECHNOLOGY CO., LTD., Beijing (CN)

( * ) Notice: Subject to any disclaimer, the term of this patent is extended or adjusted under 35 U.S.C. 154(b) by 786 days.

(21) Appl. No.: 16/977,186

(22) PCT Filed: Mar. 1, 2018

(86) PCT No.: PCT/CN2018/077748
§ 371 (c)(1),
(2) Date: Sep. 1, 2020

(87) PCT Pub. No.: WO2019/165623
PCT Pub. Date: Sep. 6, 2019

(65) Prior Publication Data
US 2021/0038207 A1 Feb. 11, 2021

(51) Int. Cl.
*A61B 17/00* (2006.01)
*A61M 25/09* (2006.01)
*D03D 11/00* (2006.01)

(52) U.S. Cl.
CPC ........ *A61B 17/00234* (2013.01); *D03D 11/00* (2013.01); *A61B 2017/00238* (2013.01);
(Continued)

(58) Field of Classification Search
CPC .......... A61B 5/6851; A61B 2562/0247; A61B 5/0215; A61B 17/00234;
(Continued)

(56) References Cited

U.S. PATENT DOCUMENTS

| 4,619,274 A | 10/1986 | Morrison |
| 7,931,603 B2 | 4/2011 | Von Malmborg et al. |
| 2014/0081244 A1 | 3/2014 | Voeller et al. |

FOREIGN PATENT DOCUMENTS

| EP | 2845620 A1 | 3/2015 |
| JP | H06-011339 A | 1/1994 |

(Continued)

OTHER PUBLICATIONS

Notice of Reasons for Refusal dated Oct. 25, 2021 received in Japanese Patent Application No. JP 2020-545715 together with an English language translation.

*Primary Examiner* — Jon Eric C Morales
(74) *Attorney, Agent, or Firm* — Scully, Scott, Murphy & Presser, P.C.

(57) ABSTRACT

Provided is a pressure guide wire, including a proximal portion (1), an intermediate portion (2) and a distal portion (12), the intermediate portion (2) is composed of one or more woven layers, wherein each woven layer includes a plurality of woven wires, the distal portion (12) includes a sensor housing (4) that holds a pressure sensor (5) and a head end assembly (11), the head end assembly (11) includes a developing spring (9) and a head end core wire (11) nested within the developing spring (9). The pressure guide wire having such a structure has good flexibility and supportability, meanwhile, the cost of the pressure guide wire can be reduced due to the low cost of the woven wire and the weaving process.

16 Claims, 5 Drawing Sheets (52) U.S. Cl.
CPC .............. *A61B 2017/00305* (2013.01); *A61B 2560/0462* (2013.01)

(58) Field of Classification Search
CPC .............. A61B 2560/0462; A61B 5/00; A61B 2562/12; A61B 5/02158; A61M 2025/09191; A61M 2025/09083; A61M 25/09; A61M 2025/09183; A61M 25/01; D03D 11/00
See application file for complete search history.

(56) References Cited

FOREIGN PATENT DOCUMENTS

| | | |
|---|---|---|
| JP | 2002-275774 A | 9/2002 |
| JP | 2003-265617 A | 9/2003 |
| JP | 2007-075531 A | 3/2007 |
| JP | 2007-511308 A | 5/2007 |
| JP | 2015-051085 A | 3/2015 |
| JP | 2015-533542 A | 11/2015 |
| JP | 2016-182213 A | 10/2016 |

PRESSURE GUIDE WIRE

TECHNICAL FIELD

The present disclosure relates to the field of medical devices, and in particular to a medical pressure guide wire.

BACKGROUND

A medical pressure guide wire can be used for minimally invasive interventional treatment of vascular lumen and non-vascular lumen, and usually includes a proximal portion and a distal portion. A part of the proximal portion is located outside the body and manipulated by an operator to make the guide wire travel along the lumen. The proximal portion usually has a relatively rigid tubular structure to provide good pushability and twistability. The distal portion usually has a soft tip portion to avoid damage to blood vessels.

In order to improve the navigability of the pressure guide wire through various tortuous lumens to reach the lesion location, an intermediate portion can also be provided between the proximal portion and the distal portion of the pressure guide wire. The intermediate portion is required to have good pushable performance and twisting control performance as well as good compliance.

A pressure guide wire configuration currently exists in which the proximal, intermediate, and distal portions are composed of an integral tube structure, wherein the tube structure is cut out to form a pattern at the intermediate portion to achieve the compliance. However, for such a solution, the pushability, twistability and compliance of the pressure guide wire are not so good. And due to the strong mutually exclusive relationship among the pushability, twistability and compliance of the pressure guide wire, it is not possible to simultaneously improve the pushability, twistability and compliance.

There is also a non-integral construction for the pressure guide wire, which includes sections made of different materials, and in which one or more sections can include an outer layer and an inner layer with different properties and/or made of different materials, etc., in order to achieve different mechanical properties of each section. However, the structure of this pressure guide wire is complicated, and there is a serious problem regarding bonding reliability when different materials are bonded together.

SUMMARY

In view of the above-mentioned problems and demands, a new type of pressure guide wire is proposed, which has good pushability, twistability, compliance and other advantages due to the presence of the following characteristics.

First, the present disclosure proposes a pressure guide wire, which includes: a proximal portion; an intermediate portion composed of one or more woven layers, each woven layer including a plurality of woven filaments; a distal portion including a head end assembly and a sensor housing accommodating a pressure sensor, the head end assembly including a development spring and a head end core wire nested within the development spring.

In traditional cognition, the woven filament is not able to provide sufficient supporting performance due to the fact that it is too thin and the pitch of the spiral structure formed by it is too small. Therefore, there has never been an attempt to use the woven filament to form the intermediate portion of the pressure guide wire. At the same time, the structure formed by the "weaving" method is often considered having no sufficient strength and tightness, so it has never been used as a segment of the pressure guide wire. However, the present patent proposes to use multiple woven filaments to form one or more spiral woven layers, in which each woven layer includes multiple woven filaments so that a woven structure with a relatively big pitch is formed by the very thin woven filaments. It has been verified by experiments that such a woven structure has good compliance and support performance. In terms of support performance, according to the subsequent supporting force test, such a woven structure has very outstanding supporting performance, even more than 10 times that of the woven filaments adopting the traditional method, and is much better than other existing support structures. At the same time, in terms of compliance, due to the soft property of the woven filaments themselves and the characteristics of the spirally weaving method, the woven structure has compliance that is far superior to the existing solutions, so that it can adapt to more complex lesion areas and better meet the needs of diagnosis and treatment. As for the intermediate portion of the existing structures, for example, a structure that achieves compliance by cutting a steel pipe to form a pattern, supporting performance at level of the present solution would be obtained at the cost of greatly compromising the compliance of the intermediate portion, seriously affecting the mechanical properties of the pressure guide wire; and its compliance is far inferior to the present solution. Moreover, since both the woven filament itself and the weaving process are cost efficient, this solution can reduce the overall cost of the pressure guide wire.

Preferably, each woven layer is formed of a plurality of woven filaments arranged in parallel closely to each other and spirally wound.

Preferably, the plurality of woven filaments is closely fitted to each other by pre-stress.

The solution in which a plurality of woven filaments are arranged in parallel closely fitting each other and are spirally wound to form a woven layer avoids a complicated manufacturing process and simple and easy to implement compared with the existing solutions described above.

Preferably, each woven layer includes 6 to 12 woven filaments.

Preferably, the diameter of woven filament is in the range of 0.01 mm to 0.1 mm.

Preferably, the pitch of each woven filament is between 0.1 mm and 1 mm.

By weaving a plurality of woven filaments at the same time, a woven structure with a large pitch is formed by very thin woven filaments, thereby overcoming the technical prejudice that the woven filaments cannot be used to make the intermediate portion of the pressure guide wire. And with the above parameters, the woven structure obtained has both good compliance and support.

Preferably, the intermediate portion includes at least two woven layers, and each two adjacent woven layers have different helical directions.

Preferably, the intermediate portion includes at least two woven layers, and different woven layers are formed of different numbers of woven filaments.

Compared with the existing solutions, the solution adopting woven filaments for weaving also has great flexibility. Because by adjusting the number and pitch of the woven filaments of each woven layer, the winding direction of each woven layer, the overall arrangement of individual woven layer, the number of woven layers and the like, the compliance and supportability of the entire woven structure can be changed, so as to be adapted to different application requirements. According to subsequent tests, it was confirmed that making the spiral directions of the woven filaments of two adjacent woven layers different will give the pressure guide wire better manipulating performance, and the operator is able to control the advancing direction of the pressure guide wire more easily.

Preferably, the intermediate portion includes at least two woven layers, and adjacent woven layers are closed to each other.

This solution further guarantees the impermeability of the woven structure, and makes the woven structure easy to manufacture and saves costs.

Preferably, the maximum outer diameters of the proximal portion, the intermediate portion and the distal portion are not more than 0.36 mm.

With this solution, a pressure guide wire with overall uniform thickness can be obtained. And the size of not more than 0.36 mm widens the application of the pressure guide wire.

Preferably, the pressure sensor is an optical fiber pressure sensor, which has an optical fiber that passes through the proximal portion, the intermediate portion, and the sensor housing so as to be connected to the pressure sensor.

Preferably, the head end assembly is connected to the sensor housing by a connector, wherein the connector is a tubular structure that is thin at both ends and thick in the middle, and wherein one of its ends is inserted into the development spring and the other end is inserted into the sensor housing.

The use of the connector of this specific configuration makes it possible that the welding of the sensor housing and the development spring is simple and reliable. However, if the development spring was directly welded to the sensor housing, a problem of weak welding would be raised.

Preferably, the proximal portion, the intermediate portion, the sensor housing, the connector, and the head end assembly are made of similar or the same material, and are welded in sequence.

Preferably, the proximal portion, the intermediate portion, the sensor housing, the connector, and the head end assembly are made of stainless steel.

The above solution avoids the problem of weak welding between different materials existed in the prior art that uses different materials to form the pressure guide wire.

Preferably, the head end core wire and the development spring have a taper of 0.124 degrees.

With this solution, the pressure guide wire is made to have a better piercing ability and a more excellent ability to pass through the complicated lesions.

Preferably, the head end core wire is made of a memory metal.

With this solution, the operator can preset the shape of the head end core wire in advance according to the travelling environment of the pressure guide wire, so that the pressure guide wire can easily pass through a specific position.

Hereinafter, preferred embodiments for implementing the present disclosure will be described in more detail with reference to the accompanying drawings, so that the features and advantages of the present disclosure can be easily understood.

BRIEF DESCRIPTION OF THE DRAWINGS

In order to explain the technical solutions of the embodiments of the patent more clearly, the drawings of the embodiments thereof will be briefly described below. Among them, the drawings are simply intended to illustrate some embodiments of the patent, rather than limiting all the embodiments thereof to this.

DETAILED DESCRIPTION OF EMBODIMENTS

In order to make the objectives, technical solutions and advantages of the technical solutions of the patent clearer, the technical solutions of the embodiments thereof will be described clearly and completely in the following with reference to the drawings of the specific embodiments of the patent. The same reference numerals in the drawings represent the same components. It should be noted that the described embodiments are part of the embodiments of this patent, but not all of them. Based on the described embodiments of the present patent, all the other embodiments obtained by those skilled in the art without creative efforts fall within the protection scope of the present patent.

Unless otherwise defined, the technical or scientific terms used herein shall be construed as the ordinary meaning understood by those with ordinary skills in the field to which the patent belongs. The terms "first", "second" and similar words used in the description and claims of this patent application do not indicate any order, quantity or priority, but are only intended to distinguish different components. Similarly, words such as "a" or "one" do not necessarily mean quantity limitation. Words such as "including", "comprising" or the like mean that the elements or objects appearing before the word encompass the elements or objects listed after the word and their equivalents, but do not exclude other elements or objects. Words such as "connected", "joined" or the like are not limited to physical or mechanical connections, but may include electrical connections, whether direct or indirect. "Up", "down", "left", "right", etc. are merely intended to indicate the relative positional relationship; when the absolute position of the described object changes, the relative positional relationship may also change accordingly.

Figure 1:
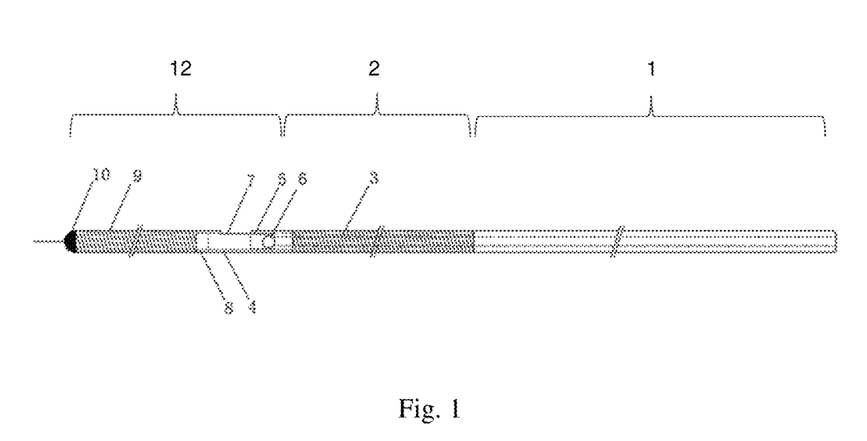
FIG. 1 is a side view of an exemplary embodiment of a pressure guide wire.

As shown in FIG. 1, a pressure guide wire according to an exemplary embodiment mainly includes a proximal portion 1, an intermediate portion 2, and a distal portion 12. The distal portion 12 mainly includes a sensor housing 4 containing a pressure sensor 5, a head end assembly including a development spring 9 and a head end core wire 11, and a connector 8 connecting the sensor housing 4 and the head end assembly.

As shown in FIG. 1, the proximal portion 1 is of an elongated tubular structure. During the diagnosis and treatment, it is positioned partially outside the body. An operator manipulates the pressure guide wire via the proximal portion so that it runs along the blood vessel or non-vascular lumen of the human body. Preferably, the length of the proximal portion 1 is 1500 mm, the outer diameter is not more than 0.36 mm, for example 0.355 mm, and the inner diameter is between 0.13 mm and 0.17 mm. The proximal portion 1 is preferably made of stainless steel, such as medical 304v stainless steel. The proximal portion 1 having the above characteristics has good pushability and twistability.

The intermediate portion 2 also has an elongated tubular structure and is arranged coaxially with the proximal portion 1. Preferably, the length of the intermediate portion 2 is less than 300 mm, for example 280 mm. The inner and outer diameters of the intermediate portion 2 are preferably the same as the proximal portion 1, that is, the outer diameter is not greater than 0.36 mm, for example, 0.355 mm, and the inner diameter is between 0.13 mm and 0.17 mm. The intermediate portion 2 is preferably made of a material similar to or the same as the proximal portion 1, for example also made of stainless steel, for example medical 304v stainless steel. This coaxial arrangement of the intermediate portion 2 and the proximal portion 1 and the selection of similar/same materials allow the two to be easily welded together.

The intermediate portion 2 is preferably composed of one or more woven layers, wherein each woven layer is formed of a plurality of woven filaments arranged in parallel closely to each other and spirally wound.

Specifically, each woven layer may include 6 to 12 woven filaments, such as 6, 8, or 12, and the like. The diameter of each woven filament is in the range of 0.01 mm to 0.1 mm. Preferably, the pitch of the woven filaments is approximately 0.1 mm to 1 mm, more preferably 0.4 mm.

In the traditional cognition, the woven filament is too thin and the pitch of the helical structure thus formed is too small to provide sufficient supporting performance. Therefore, there has never been an attempt to use the woven filament to form the intermediate portion of the pressure guide wire. At the same time, the structure formed by the "weaving" method is often considered not having sufficient strength and tightness, so it has never been used as a segment of the pressure guide wire. However, this patent proposes to use multiple woven filaments to form one or more spirally woven layers, in which each woven layer includes multiple woven filaments so that a woven structure with a relatively big pitch is formed by the very thin woven filaments. It has been verified by experiments that such a woven structure has good compliance and support. In terms of support, according to the subsequent supporting force test, such a woven structure has very outstanding supporting performance, even more than 10 times that of the woven filaments adopting the traditional method, and is much more excellent than other existing support structures. At the same time, in terms of compliance, due to the soft property and the characteristics of the spirally weaving method, the woven structure has compliance that is far superior to the existing solutions, so that it can adapt to more complex lesion areas and better meet the needs of diagnosis and treatment. As for the intermediate portion of the existing structures, for example, a structural solution that achieves compliance by cutting a steel pipe into a pattern, if they ever obtained the supporting performance of the present solution, the compliance of the intermediate portion would have been compromised greatly, which seriously affects the mechanical properties of the pressure guide wire; and its compliance is far more different than the present solution. In addition, compared with the existing solutions, the present solution adopting woven filaments for weaving also has great flexibility. Because by adjusting the number and pitch of the woven filaments of each woven layer, the winding direction of each woven layer, the overall arrangement of individual woven layer, the number of woven layers and the like, the compliance and supportability of the entire woven structure can be changed, so as to adapt to different application requirements. Moreover, since both the woven filament itself and the weaving process are cost efficient, this solution can reduce the overall cost of the pressure guide wire.

According to the above-mentioned concept provided by the present disclosure, the intermediate portion 2 may include one or more woven layers, each woven layer being composed of a plurality of woven filaments. For a solution including at least two woven layers, different woven layers may be formed of the same or different numbers of woven filaments.

According to the above-mentioned concept provided by the present disclosure, the winding direction of the woven filaments of each woven layer may be left-handed or right-handed. For a single-layer woven structure, the direction of the woven filament may be left-handed or right-handed. For a solution including at least two woven layers, the winding directions of different woven layers may be the same or different. Preferably, it is provided that two of those adjacent woven layers have different spiral directions. More preferably, the spiral directions of the woven filaments of each two adjacent woven layers are different, that is, the weaving directions changes sequentially from the innermost layer to the outermost layer.

Figure 6:
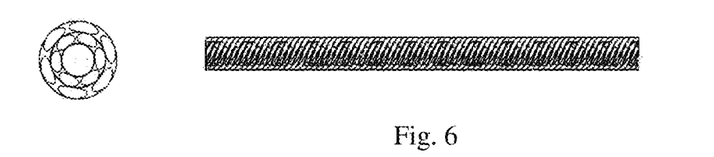
FIG. 6 is an exemplary embodiment of an intermediate portion having a double-layer woven structure, which shows a cross-sectional view and a side view of the intermediate portion.
Figure 7:
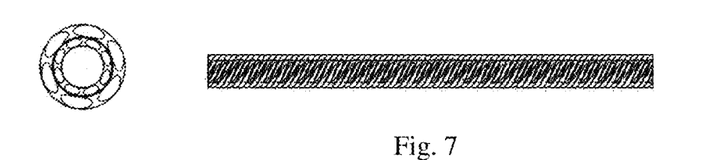
FIG. 7 is an exemplary embodiment of an intermediate portion having a double-layer woven structure, which shows a cross-sectional view and a side view of the intermediate portion.
Figure 8:
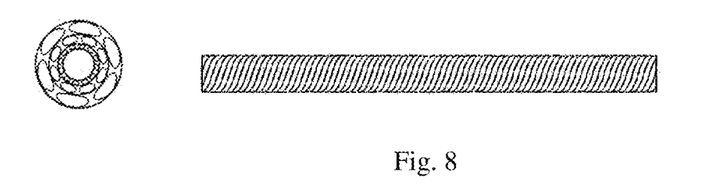
FIG. 8 is an exemplary embodiment of an intermediate portion having a three-layer woven structure, which shows a cross-sectional view and a side view of the intermediate portion.
Figure 9:
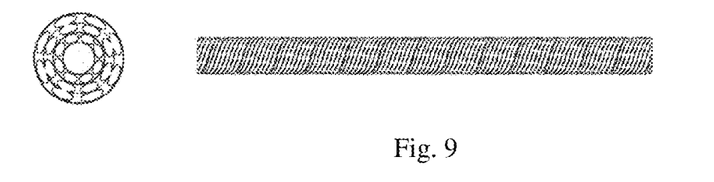
FIG. 9 is an exemplary embodiment of an intermediate portion having a three-layer woven structure, which shows a cross-sectional view and a side view of the intermediate portion.

FIGS. 5-9 show several specific embodiments of the intermediate portion 2. FIGS. 5A-C show the intermediate portion with only one woven layer. In the embodiment of FIG. 5A, the woven layer is formed by spirally winding six parallel woven filaments. In the embodiment of FIG. 5B, the woven layer is formed by spirally winding eight parallel woven filaments. In the embodiment of FIG. 5C, the woven layer is formed by spirally winding twelve parallel woven filaments. FIGS. 6-7 show the intermediate portion with two woven layers. In the embodiment of FIG. 6, the inner and outer woven layers are both formed by spirally winding six parallel woven filaments. And in the embodiment of FIG. 6, the inner woven layer is formed by spirally winding eight parallel woven filaments and the outer woven layer is also formed by spirally winding eight parallel woven filaments. For the solutions shown in FIGS. 6-7, preferably, the weaving directions of the inner and the outer woven layers are different. FIG. 8 shows the intermediate portion with three woven layers, wherein the three woven layers from the inside to the outside are formed by 12, 8, and 6 woven filaments, respectively. For this solution, it is preferable to make the weaving directions of at least one pair of adjacent woven layers different; more preferably, the weaving direction changes sequentially from the innermost layer to the outermost layer. FIG. 9 shows the intermediate portion with four woven layers, wherein all four woven layers are formed by spirally winding six woven filaments. For this solution, it is preferable to make the weaving directions of the adjacent woven layers different. More preferably, the weaving directions changes sequentially from the innermost layer to the outermost layer. According to subsequent tests, it is confirmed that the manipulating performance of the pressure guide wire with this configuration is better.

Due to the fact that a plurality of woven filaments arranged in parallel and spirally wound are closely fitted to each other, there is no gap between adjacent woven filaments. The effect of this close-fitting arrangement can be achieved by the pre-stress introduced during the weaving process of the woven filaments. That is, when forming the woven layer, a mandrel is provided on which a plurality of woven filaments arranged in parallel are closely wound. During winding, a pre-stress for twisting around itself is introduced to each woven filament, so that the adjacent woven filaments closely fit together under the effect of the pre-stress after the mandrel is removed.

As for an intermediate portion including two or more woven layers, adjacent woven layers are arranged so as to be closely fit. The effect of this close-fitting arrangement effect can be achieved by the over-tight winding process of the woven filaments. That is, after a woven layer (referred to as the first woven layer) is formed, on which woven filaments for forming another woven layer (referred to as a second woven layer) are then closely wound, a pre-stress with contracting tendency is thus formed in the woven filaments of the second woven layer. Therefore the second woven layer is closely wound around the first woven layer.

Figure 2:
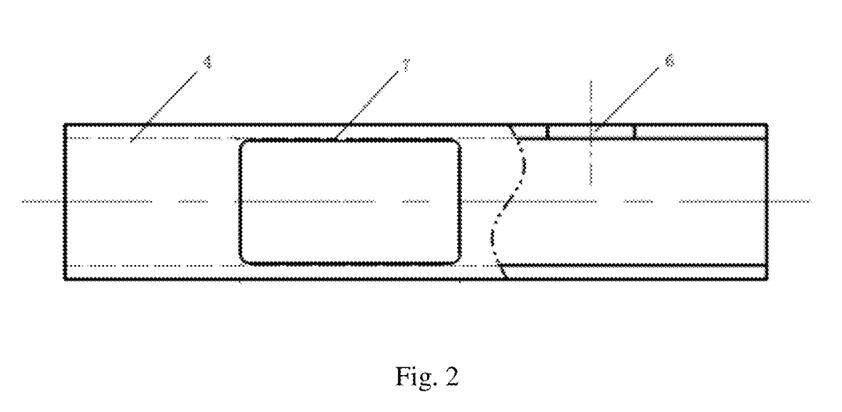
FIG. 2 is a schematic top view of a sensor housing.
Figure 3:
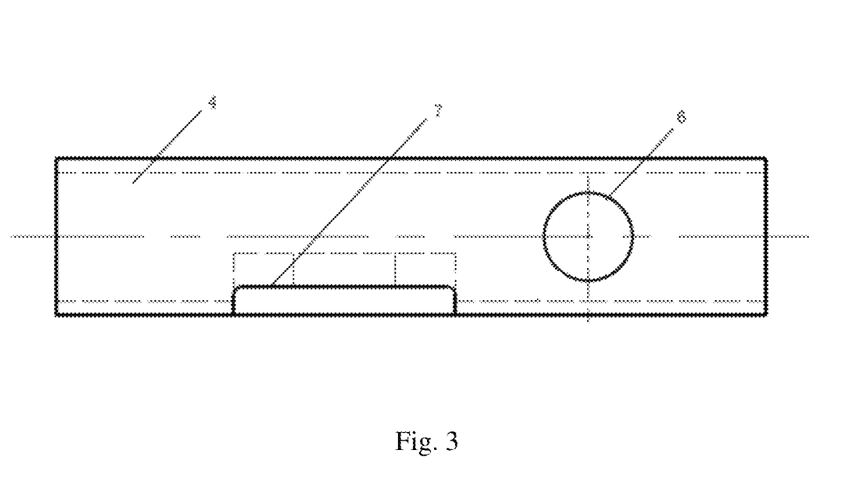
FIG. 3 is a schematic side view of the sensor housing.

FIGS. 2 and 3 respectively show an exemplary embodiment of the sensor housing 4 from different perspectives. The sensor housing 4 also has a substantially tubular structure. And its outer diameter is close to those of the proximal portion 1 and the intermediate portion 2, that is, not more than 0.36 mm, for example, 0.355 mm, and its inner diameter is not more than 0.28 mm. The length of the sensor housing 4 is preferably not more than 2.5 mm, for example 1.6 mm. The sensor housing 4 is preferably made of a material similar to or the same as the proximal portion 2, for example also made of stainless steel, for example medical 304v stainless steel, so as to ensure the welding reliability with the intermediate portion 2.

The pressure sensor 5 is provided in the sensor housing 4. Preferably, the pressure sensor 5 is an optical fiber pressure sensor and has an optical fiber as a sensor communication device that passes through the proximal portion 1, the intermediate portion 2, and the sensor housing 4 so as to be connected to the pressure sensor 5.

The sensor housing 4 is provided with a sensing window 7 through which blood pressure is applied to the sensor 5 to measure the pressure of blood in the blood vessel. Preferably, the sensing window 7 is a square one, and its size preferably has a length of 0.5 mm, a width of 0.27 mm, and a chamfer of R0.02 mm. The sensing window 7 is located no more than 0.6 mm from the proximal portion of the development spring 9.

The sensor housing 4 may also be provided with an opening 6 that can be used as an operating opening for installing and fastening the pressure sensor 5. For example, in the manufacturing process of installing the pressure guide wire, the opening 6 can be used to fasten the pressure sensor 5 to the sensor housing 4 by glue in a viscous manner. Preferably, the opening 6 is a substantially circular one, and its diameter is preferably not more than 0.2 mm. The center of the opening 6 is located no more than 1.5 mm from the development spring 9. Preferably, the center of the opening 6 and the center of the sensing window 7 differ by about 90 degrees in the circumferential direction of the sensor housing.

The head end assembly includes a development spring 9, a head end core wire 11 nested in the development spring 9, and a head end portion 10 welded to the development spring 9 and the head end core wire 11.

Figure 10:
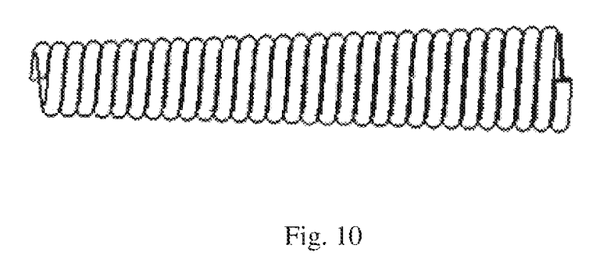
FIG. 10 is a schematic diagram of a development spring.

The development spring 9 is used to locate the pressure guide wire in the blood vessel to improve the visibility of the guide wire in the diseased blood vessel or body cavity during the treatment. For this, the development spring 9 may be composed of a developing material, or coated with a developing material. Meanwhile, the spring structure of the development spring 9 has an excellent ability of passing through a complicated lesion area, and is capable to improve the shaping ability and shaping retention of the tip of the guide wire. FIG. 10 shows an exemplary embodiment of the development spring 9. The developing spring 9 is a tapered type coil spring. Preferably, its length is 35 mm and its outer diameter is not more than 0.36 mm, for example, 0.355 mm.

Figure 11A:
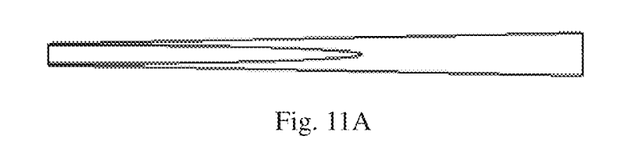
FIGS. 11A and 11B are schematic views of a head end core wire inserted inside the development spring.
Figure 11B:
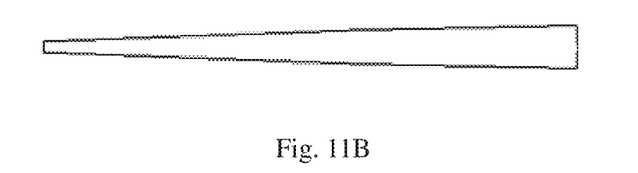

The head end core wire 11 is nested by the development spring, and is preferably made of a memory metal. Therefore, the operator can preset the shape of the head end core wire in advance according to the travelling environment of the pressure guide wire, so that the pressure guide wire can easily pass through a specific position. In the exemplary configuration shown in FIGS. 11A-11B, the head end core wire 11 has an elongated and tapered configuration. Preferably, the development spring 9 and the head end core wire 11 are designed to have a taper of 0.124 degrees, so that the pressure guide wire has a certain piercing ability and a more excellent ability to pass through the complicated lesions.

The head end core wire 11 has a head end portion 10 in one piece with the head end core wire, or the head end portion 10 may be welded to the head end core wire 11 later. The head end 10 is shown in FIG. 1 and has a smoothly transitioned shape, such as a streamlined shape, a parabolic shape, a smoothly transitioned stepped shape and the like, to facilitate passage through a tortuous lumen.

The head end assembly with the above characteristics makes it possible that the head end of the pressure guide wire is softer and has better shape retention, and will not generate permanent deformation after being stressed. Thus it ensures that the pressure guide wire can be applied to more lesions and effectively alleviates the economic pressure of patients.

Figure 4:
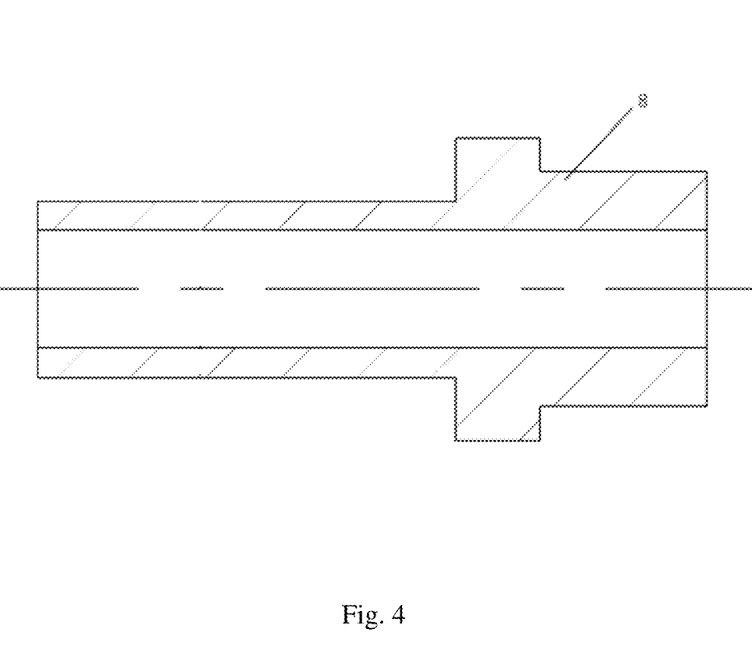
FIG. 4 is a schematic side view of a connector.
Figure 5A:
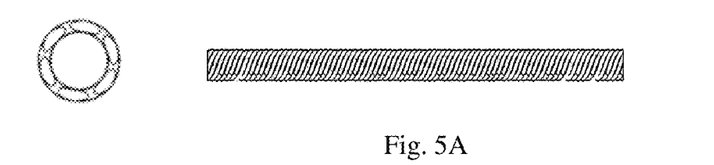
FIG. 5A-C are exemplary embodiments of an intermediate portion having a single-layer woven structure, each of which shows a cross-sectional view and a side view of the intermediate portion.
Figure 5B:
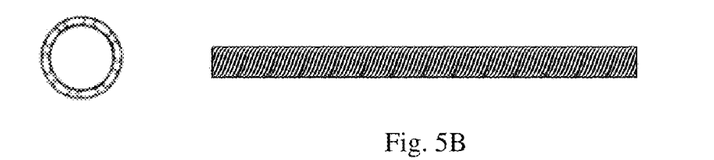
Figure 5C:
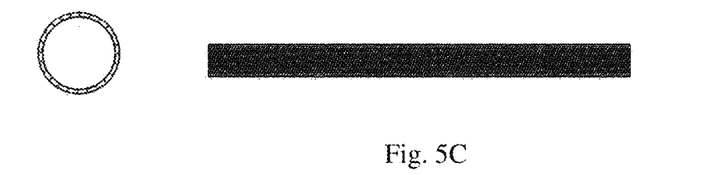

According to a preferred embodiment, the connector 8 is used to weld the development spring 9 and the sensor housing 4 together. As shown in FIG. 4, the connector 8 is a tubular structure that is thin at both ends and thick in the middle. One of its ends is inserted and welded to the development spring 9 and the other end is inserted and welded to the sensor housing 4. The use of the connector 8 of this specific configuration makes it possible that the welding of the sensor housing 4 and the development spring 9 is simple and reliable. However, if the development spring 9 was directly welded to the sensor housing 4, a problem of weak welding would be raised.

According to a preferred embodiment, the connector 8 has a length of 0.8 mm and an inner diameter of 0.14 mm, wherein the end for connecting the development spring has a length of 0.5 mm and an outer diameter of 0.21 mm, and the end for connecting the sensor housing has a length of 0.2 mm and an outer diameter of 0.27 mm. The outer diameter of the intermediate portion is not more than 0.36 mm.

Based on the above content, according to the present disclosure, preferably, the maximum outer diameter of the proximal portion, the intermediate portion and the distal portion are made substantially same and not more than 0.36 mm. In addition, the proximal portion, the intermediate portion, the sensor housing, the connector, and the head end assembly are made of similar or the same material (preferably stainless steel), and are welded in sequence. In this way, it is possible to obtain a pressure guide wire which is easy to be manufactured by welding and has more expanded uses.

The exemplary implementations of the pressure guide wire proposed by the present patent have been described in detail above with reference to preferred embodiments. However, those skilled in the art can understand that the above specific embodiments can be implemented to make various changes and modifications without departing from the concept of the present patent, and various technical features and structures proposed in the present patent can be combined in various ways without going beyond the protection scope of the present patent, which is determined by the appended claims.

LIST OF REFERENCE NUMBERS 1 proximal portion
2 intermediate portion
3 optical fiber
4 sensor housing
5 sensor
6 opening
7 sensing window
8 connector
9 development spring
10 head end portion
11 head end core wire
12 distal portion

What is claimed is:

1. A pressure guide wire, characterized in that it includes:
a proximal portion;
an intermediate portion, which is composed of one or more woven layers, wherein each woven layer includes a plurality of woven filaments;
a distal portion, which includes a sensor housing accommodating a pressure sensor and a head end assembly, the head end assembly including a development spring and a head end core wire nested within the development spring.

2. The pressure guide wire according to claim 1, characterized in that each woven layer is formed of a plurality of woven filaments arranged in parallel closely to each other and spirally wound.

3. The pressure guide wire according to claim 2, characterized in that the plurality of woven filaments are closely fitted to each other by pre-stress.

4. The pressure guide wire according to claim 1, characterized in that each woven layer includes 6 to 12 woven filaments.

5. The pressure guide wire according to claim 1, characterized in that the diameter of woven filament is in the range of 0.01 mm to 0.1 mm.

6. The pressure guide wire according to claim 1, characterized in that the pitch of each woven filament is between 0.1 mm and 1 mm.

7. The pressure guide wire according to claim 1, characterized in that the intermediate portion includes at least two woven layers, and each two adjacent woven layers have different spiral directions.

8. The pressure guide wire according to claim 1, characterized in that the intermediate portion includes at least two woven layers, and different woven layers are formed of different numbers of woven filaments.

9. The pressure guide wire according to claim 1, characterized in that the intermediate portion includes at least two woven layers, and adjacent woven layers are closed to each other.

10. The pressure guide wire according to claim 1, characterized in that the maximum outer diameters of the proximal portion, the intermediate portion and the distal portion are not more than 0.36 mm.

11. The pressure guide wire according to claim 1, characterized in that the pressure sensor is an optical fiber pressure sensor, which has an optical fiber that passes through the proximal portion, the intermediate portion, and the sensor housing so as to be connected to the pressure sensor.

12. The pressure guide wire according to claim 1, characterized in that the head end assembly is connected to the sensor housing by a connector, wherein the connector is a tubular structure that is thin at both ends and thick in the middle, and wherein one of its ends is inserted into the development spring and the other end is inserted into the sensor housing.

13. The pressure guide wire according to claim 12, characterized in that the proximal portion, the intermediate portion, the sensor housing, the connector, and the head end assembly are made of similar or the same material, and are welded in sequence.

14. The pressure guide wire according to claim 12, characterized in that the proximal portion, the intermediate portion, the sensor housing, the connector, and the head end assembly are made of stainless steel.

15. The pressure guide wire according to claim 1, characterized in that the head end core wire and the development spring have a taper of 0.124 degrees.

16. The pressure guide wire according to claim 1, characterized in that the head end core wire is made of a memory metal.

* * * * *